(12) United States Patent
Velculescu et al.

(10) Patent No.: US 10,815,522 B2
(45) Date of Patent: Oct. 27, 2020

(54) GENOMIC ALTERATIONS IN THE TUMOR AND CIRCULATION OF PANCREATIC CANCER PATIENTS

(71) Applicant: The Johns Hopkins University, Baltimore, MD (US)

(72) Inventors: Victor Velculescu, Dayton, MD (US); Mark Sausen, Baltimore, MD (US); Vilmos Adleff, Baltimore, MD (US); Jillian Phallen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/552,076

(22) PCT Filed: Feb. 18, 2016

(86) PCT No.: PCT/US2016/018450
§ 371 (c)(1),
(2) Date: Aug. 18, 2017

(87) PCT Pub. No.: WO2016/134136
PCT Pub. Date: Aug. 25, 2016

(65) Prior Publication Data
US 2018/0155770 A1   Jun. 7, 2018

Related U.S. Application Data

(60) Provisional application No. 62/118,604, filed on Feb. 20, 2015.

(51) Int. Cl.
*C12Q 1/6827* (2018.01)
*C12Q 1/6886* (2018.01)
*C12Q 1/6816* (2018.01)

(52) U.S. Cl.
CPC ......... *C12Q 1/6827* (2013.01); *C12Q 1/6816* (2013.01); *C12Q 1/6886* (2013.01); *C12Q 2600/106* (2013.01); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS 6,582,908 B2 * 6/2003 Fodor ................. B01J 19/0046
435/288.3
2013/0210900 A1   8/2013 Vogelstein et al.

OTHER PUBLICATIONS

Balakrishnan et al. Cancer Research. 2007. 67(7): 3545-3550.*
Free Dictionary definition for "Testing," available via URL: <.thefreedictionary.com/testing>, printed on Nov. 26, 2018.*
Biankin et al Nature. Nov. 2012. 491: 399-405 and Supplementary Tables 5 and 8.*
Uemura et al J Gastroenterol 2004. 39: 56-60.*
Olsen et al. Am J Clinical Oncology. 2009. 32(2): 115-121.*
Bettegowda, C. et al. "Detection of circulating tumor DNA in early- and late-stage human malignancies," *Sci Transl Med* 6, 224ra24 (2014).
Balakrishnan et al., Novel somatic and germline mutations in cancer candidate genes in glioblastoma, melanoma, and pancreatic carcinoma Cancer Research, vol. 67, No. 8, pp. 3545-3550 (2007) See abs tract: pp. 3545-3547: and Tables 1-2.
Biankin, A.V. et al., "Pancreatic cancer genomes reveal aberrations in axon guidance pathway genes," Nature 491, 399-405 (2012).
Gupta et al., "Abstract 21.74:MLL3 act as a tumor suppressor gene in pancreatic cancer," *Cancer Research*, vol. 72, Abstract No. 2174 (2012).
Cooper, G.M. et al., "Distribution and intensity of constraint in mrunmalian genomic sequence," *Genome Res* 15, 901-13 (2005).
Fogelman, D.R. et al. Evidence for the efficacy of Iniparib, a PARP-1 inhibitor, in BRCA2-associated pancreatic cancer. Anticancer Res 31. 1417-20 (2011).
Fong, P.C. et al., "Inhibition of poly(ADP-ribose) polymeiuse in tumors from BRCA mutation carriers," *N Engl J Med* 361, 123-34 (2009).
Forbes, S.A. et al. "COSMIC: mining complete cancer genomes in the Catalogue of Somatic Mutations in Cancer" *Nucleic Acids Res* 39, D945-50 (2011).
Goyama et al., "NF-KB: A Coordinator for Epigenetic Regulation by MLL," *Cancer Cell* 24, 401-2 (2013).
Gupta et al., "MLL3 act as a tumor suppressor gene in pancreat ic cancer," *Cancer Research*, vol. 72, Abstract No. 2174 (2012).
Iacobuzio-Donahne et al., "Genetic basis of pancreas cancer development and progression: insights from whole-exome and whole-genome sequencing," *Clin Cancer Res* 18, 4257-65 (2012).
International Search Report and Written Opinion in International Application No. PCT/US2016/018450, dated Aug. 8, 2016, 11 pages.

(Continued)

*Primary Examiner* — Carla J Myers
(74) *Attorney, Agent, or Firm* — Fish & Richardson P.C.

(57) ABSTRACT

Pancreatic adenocarcinoma has the worst overall mortality of any solid tumor, with only 7% of patients surviving after 5 years. To evaluate the clinical implications of genomic alterations in this low cellularity tumor type, we deeply sequenced the genomes of 101 enriched pancreatic adenocarcinomas from patients who underwent potentially curative resections and used non-invasive approaches to examine tumor specific mutations in the circulation of these patients. These analyses revealed somatic mutations in chromatin regulating genes including MLL and ARID1A in 20% of patients that were associated with improved survival. Liquid biopsy analyses of cell free plasma DNA revealed that 43% of patients with localized disease had detectable circulating tumor DNA (ctDNA) in their blood at the time of diagnosis. Detection of ctDNA after resection predicted clinical relapse and poor outcome, and disease recurrence by ctDNA was detected 6.5 months earlier than with standard CT imaging.

9 Claims, 12 Drawing Sheets

(56) References Cited

OTHER PUBLICATIONS

Jiao, Y. et al. DAXX/ATRX, MEN1, and mTOR pathway genes are frequently altered in pancreatic neuroendocrine tumors. Science 331, 1199-203 (2011).

Johansen et al., Comparative circulating tumor DNA levels for KRAS mutations in patients with nonresectable pancreatic cancer Journal of Clinical Oncology, vol. 33, Supplement No. 3, Abstract No. 288 (Jan. 2015).

Jones, S. et al. Core signaling pathways in human pancreatic cancers revealed by global genomic analyses. Science 321, 1801-6 (2008).

Jones, S. et al., "Somatic mutations in the chromatin remodeling gene ARID1A occur in several tumor types," *Hum Mutat* 33, 100-3 (2012).

Newman et al., "An ultrasensitive method for quantitating circulating tumor DNA with broad patient coverage," *Nat Med* 20, 548-54 (2014).

Paulson et al., "Therapeutic advances in pancreatic cancer," *Gastroenterology* 144, 1316-26 (2013).

Shain et al., "Convergent structural alterations define SWItch/Sucrose NonFermentable (SWI/SNF) chromatin remodeler as a central tumor suppressive complex in pancreatic cancer," PNAS, vol. 109, No. 5. pp. E252-E259 (2012).

Popovic et al., "Emerging epigenetic targets and therapies in cancer medicine," *Cancer Discov* 2(5), 405-13 (2012).

Rammathan, R.K. et al. Low overexpression of HER-2/neu in advanced colorectal cancer limits the usefulness of trastuzumab (Herceptin) and irinotecan as therapy. A phase II Trial. *Cancer Invest* 22, 858-65 (2004).

Sausen et al., "Clinical Implications of genomic alterations in the tumour and circulation of pancreatic cancer patients," Nature Communications vol. 6. No. 7686 (2015).

Sausen, M. et al., "Integrated genomic analyses identidentify ARID1A and ARID1B alterations in the childhood cancer neuroblastoma," *Nat Genet* 45, 12-7 (2013).

Shain et al., "Convergent structural alterations define SWItch/Sucrose NonFerment able (SW 1/SNF) chromatin remodeler as a central tumor suppressive complex in pancreatic," *cancer PNAS*, vol. 109, No. 5, pp. E252-E259 (2012).

Siegel et al., "Cancer statistics, 2013." CA Cancer J Clin 63, 11-30 (2013).

Siegel et al., "Cancer statistics, 2015," CA Cancer J Clin 65, 5-29 (2015).

Sorscher, S.M. Marked response to single agent trastuzumab in a patient with metastatic HER-2 gene amplified rectal cancer. *Cancer Invest* 29, 456-9 (2011).

Van der Heijden, M.S. et al., "In vivo therapeutic responses contingent on Fanconi anemia/BRCA2 status of the tumor," *Clin Cancer Res* 11, 7508-15 (2005).

Villrurnel, M.C. et al., "Personalizing cancer treatment in the age of global genomic analyses: P ALB2 gene mutations and the response to DNA damaging agents in pancreatic cancer," *Mol Cancer Ther* 10, 3-8 (2011).

Wang et al, Whole-exome sequencing of human pancreatic cancers and characterization of genomic instability caused by MLHI haploinsufficiency and complete deficiency, *Genome Research*, vol. 22, pp. 208-219 (2012).

\* cited by examiner

Fig. 4

Table 1. Clinical Actionability of Genetic Alterations in Pancreatic Cancer*

| Clinical Actionability | Total Cases | Fraction of Cases (n=101) |
|---|---|---|
| FDA-Approved Therapy (Pancreatic Cancer) | 0 (0) | 0% (0%) |
| FDA-Approved Therapy (Another Indication) | 6 (6) | 6% (6%) |
| Published Trial (Pancreatic Cancer) | 0 (0) | 0% (0%) |
| Published Trial (Another Indication) | 27 (27) | 27% (27%) |
| Active Trial (Pancreatic Cancer) | 96 (17) | 95% (17%) |
| All Types Combined | 98 (38) | 97% (38%) |

*Figures in parentheses exclude alterations observed in *KRAS* and *TP53*

Supplementary Figure 1. Schematic of Mutations in MLL and ARID1A Proteins.

Supplementary Figure 2. Kaplan Meier Progression-Free Survival Analysis of MLL and Chromatin Regulator Mutations.

Supplementary Figure 3. Prediction of Recurrence using ctDNA Detected at Baseline.

Fig. 8

Supplementary Table 1. Summary of Genes Analyzed Using Targeted Cancer Gene Sequencing

| ABL1 | CREBBP | IDH1 | MSH6 | PTPN11 |
|---|---|---|---|---|
| AKT1 | CTNNB1 | IDH2 | MYC | RB1 |
| AKT2 | DAXX | IGF1R | MYCN | RET |
| ALK | DNMT3A | IGF2R | MYD88 | RNF43 |
| APC | EGFR | IKZF1 | NF1 | ROS1 |
| AR | ERBB2 | JAK1 | NF2 | RUNX1 |
| ARID1A | ERBB3 | JAK2 | NOTCH1 | SF3B1 |
| ARID1B | ERBB4 | JAK3 | NOTCH2 | SMAD2 |
| ASXL1 | EZH2 | KDR | NOTCH3 | SMAD3 |
| ATM | FBXW7 | KIT | NOTCH4 | SMAD4 |
| ATRX | FGFR1 | KRAS | NPM1 | SMARCB1 |
| BAP1 | FGFR2 | MAML1 | NRAS | SMO |
| BRAF | FGFR3 | MDM2 | PALB2 | STAG2 |
| BRCA1 | FGFR4 | MDM4 | PAX5 | STK11 |
| BRCA2 | FLT3 | MED12 | PBRM1 | TET2 |
| CBL | FOXL2 | MEN1 | PDGFRA | TGFBR2 |
| CCND1 | GATA1 | MET | PDGFRB | TNFAIP3 |
| CCNE1 | GATA2 | MLH1 | PIK3CA | TP53 |
| CDH1 | GNA11 | MLL | PIK3R1 | TPMT |
| CDK4 | GNAQ | MLL2 | PMS2 | TSC1 |
| CDK6 | GNAS | MLL3 | PRSS1 | TSC2 |
| CDKN2A | HNF1A | MPL | PTCH1 | TSHR |
| CEBPA | HRAS | MSH2 | PTEN | VHL |
|  |  |  |  | WT1 |

Fig. 9

Supplementary Table 4. Summary of Somatic Sequence Alterations Identified

| Case ID | Gene Symbol | Gene Description | Transcript Accession | Nucleotide (hg18, genomic) | Amino Acid (protein) | Mutation Type | Consequence | Mutant Tags (%) | Analysis Completed |
|---|---|---|---|---|---|---|---|---|---|
| CGPA223 | MLL3 | myeloid/lymphoid or mixed-lineage leukemia 3 | CCDS5931.1 | chr7_151480485-151480485_C_G | 3704>L | Substitution | Nonsynonymous coding | 11% | Exome analysis |
| CGPA225 | MLL | myeloid/lymphoid or mixed-lineage leukemia (trithorax homolog, Drosophila) | CCDS31686.1 | chr11_117854039-117854039_G_C | 1161C>S | Substitution | Nonsynonymous coding | 41% | Exome analysis |
| CGPA228 | ARID1A | AT rich interactive domain 1A (SWI-like) | CCDS285.1 | chr1_26928798-26928798_C_T | 403Q>X | Substitution | Nonsense | 15% | Exome analysis |
| CGPA228 | MLL | myeloid/lymphoid or mixed-lineage leukemia (trithorax homolog, Drosophila) | CCDS31686.1 | chr11_117847769-117847769_C_A | 229P>T | Substitution | Nonsynonymous coding | 18% | Exome analysis |
| CGPA229 | ARID1A | AT rich interactive domain 1A (SWI-like) | CCDS285.1 | chr1_26979465-26979465_C | NA | Insertion | Frameshift | 26% | Exome analysis |
| CGPA229 | MLL2 | histone-lysine N-methyltransferase MLL2 | NM_003482 | chr12_47718147-47718147_G_A | 5087R>W | Substitution | Nonsynonymous coding | 28% | Exome analysis |
| CGPA231 | MLL3 | myeloid/lymphoid or mixed-lineage leukemia 3 | CCDS5931.1 | chr7_151515732-151515732_C_T | NA | Substitution | Splice site donor | 45% | Exome analysis |
| CGPA236 | MLL2 | histone-lysine N-methyltransferase MLL2 | NM_003482 | chr12_47729834-47729834_A | NA | Insertion | Frameshift | 30% | Exome analysis |
| CGPA240 | MLL3 | myeloid/lymphoid or mixed-lineage leukemia 3 | CCDS5931.1 | chr7_151576224-151576224_G_A | 743P>L | Substitution | Nonsynonymous coding | 14% | Exome analysis |
| CGPA248 | ARID1A | AT rich interactive domain 1A (SWI-like) | CCDS285.1 | chr1_26978312-26978312_A_G | 1779E>G | Substitution | Nonsynonymous coding | 44% | Targeted Analysis |
| CGPA255 | ARID1A | AT rich interactive domain 1A (SWI-like) | CCDS285.1 | chr1_26978589-26978589_C_G | 1871H>Q | Substitution | Nonsynonymous coding | 43% | Targeted Analysis |
| CGPA255 | MLL3 | myeloid/lymphoid or mixed-lineage leukemia 3 | CCDS5931.1 | chr7_151476195-151476195_G_A | 4524R>W | Substitution | Nonsynonymous coding | 5% | Targeted Analysis |
| CGPA256 | ARID1A | AT rich interactive domain 1A (SWI-like) | CCDS285.1 | chr1_26895595-26895595_GGC | 38E>EA | Insertion | In-frame insertion | 33% | Targeted Analysis |
| CGPLP420 | MLL3 | myeloid/lymphoid or mixed-lineage leukemia 3 | CCDS5931.1 | chr7_151686522-151686522_TC | NA | Insertion | Frameshift | 4% | Targeted Analysis |
| CGPLP433 | MLL2 | histone-lysine N-methyltransferase MLL2 | NM_003482 | chr12_47711653-47711653_T | NA | Insertion | Frameshift | 6% | Targeted Analysis |
| CGPLP435 | ARID1A | AT rich interactive domain 1A (SWI-like) | CCDS285.1 | chr1_26960135-26960135_C_T | 708Q>X | Substitution | Nonsense | 12% | Targeted Analysis |
| CGPLP433 | MLL2 | histone-lysine N-methyltransferase MLL2 | NM_003482 | chr12_47731362-47731362_G | NA | Deletion | Frameshift | 12% | Targeted Analysis |
| CGPLP443 | MLL3 | myeloid/lymphoid or mixed-lineage leukemia 3 | CCDS5931.1 | chr7_151601824-151601824_T | NA | Insertion | Frameshift | 3% | Targeted Analysis |
| CGPLP463 | MLL2 | histone-lysine N-methyltransferase MLL2 | NM_003482 | chr12_47722327-47722327_G_A | 1974T>M | Substitution | Nonsynonymous coding | 14% | Targeted Analysis |
| CGPLP474 | ARID1A | AT rich interactive domain 1A (SWI-like) | CCDS285.1 | chr1_26973560-26973560_G_A | 1418A>T | Substitution | Nonsynonymous coding | 4% | Targeted Analysis |
| CGPLP474 | ARID1A | AT rich interactive domain 1A (SWI-like) | CCDS285.1 | chr1_26974706-26974706_C_A | 1682A>E | Substitution | Nonsynonymous coding | 5% | Targeted Analysis |
| CGPLP478 | MLL3 | myeloid/lymphoid or mixed-lineage leukemia 3 | CCDS5931.1 | chr7_151510210-151510210_G_A | 1808R>X | Substitution | Nonsense | 29% | Targeted Analysis |
| CGPLP485 | ARID1A | AT rich interactive domain 1A (SWI-like) | CCDS285.1 | chr1_26972534-26972534_C_T | 1275E>X | Substitution | Nonsense | 14% | Targeted Analysis |
| CGPLP485 | ARID1A | AT rich interactive domain 1A (SWI-like) | CCDS285.1 | chr1_26978518-26978518_G | NA | Deletion | Frameshift | 12% | Targeted Analysis |
| CGPLP488 | ARID1A | AT rich interactive domain 1A (SWI-like) | CCDS285.1 | chr1_26979254-26979254_TT | NA | Insertion | Frameshift | 9% | Targeted Analysis |

Fig. 10

Supplementary Table 5. Recurrent Sequence Alterations in Pancreatic Ductal Adenocarcinoma*

| Gene Name | Total Cases with Somatic Mutation | Prevalence in Study Population | Corrected p value |
|---|---|---|---|
| ARID1A | 9 | 9% | p<0.0001 |
| CDKN2A | 18 | 18% | p<0.0001 |
| KRAS | 89 | 88% | p<0.0001 |
| MLL3 | 7 | 7% | 0.0440 |
| SMAD4 | 29 | 29% | p<0.0001 |
| TGFBR2 | 7 | 7% | p<0.0001 |
| TP53 | 78 | 77% | p<0.0001 |

*p values were calculated using the binomial test adjusted for background mutation rate, gene sizes, and corrected for multiple comparisons as described in the Online Methods.

Fig. 11
Supplementary Table 7. Analysis of Clinical and Genetic Features of Pancreatic Adenocarcinoma

| Clinical Characteristic | N | Chromatin Remodeling Genes (MLL, MLL2, MLL3) | | p value |
|---|---|---|---|---|
| | | Mutant | Wild-Type | |
| Total Patients | 101 | 14 | 87 | |
| Age at Diagnosis (years) | 101 | 69.6±9.6 | 66.3±9.3 | 0.24 |
| Gender | | | | 0.30 |
|   Male | 63 | 7 | 56 | |
|   Female | 38 | 7 | 31 | |
| Tumor Stage | | | | 0.79 |
|   IIA | 19 | 3 | 16 | |
|   IIB | 82 | 11 | 71 | |
| Tumor Size (cm) | 99 | 3.4±1.02 | 3.35±1.67 | 0.90 |
| Differentiation | | | | 0.81 |
|   Poor | 41 | 6 | 35 | |
|   Moderate | 38 | 4 | 34 | |
|   Well | 19 | 3 | 16 | |
| Adjuvant Therapy | | | | 0.79 |
|   Yes | 87 | 12 | 75 | |
|   No | 12 | 2 | 10 | |

Fig. 12
Supplementary Table 8. Cox Multivariable Analysis of Overall Survival for Mutations in MLL and Chromatin Regulator Genes

| Characteristic | Group | HR (95% CI) | p value | HR (95% CI) | p value |
|---|---|---|---|---|---|
| Age | | 1.013 (0.981-1.047) | 0.424 | 1.018 (0.984-1.052) | 0.302 |
| Stage | Stage IIA | 1 | 0.285 | 1 | 0.414 |
| | Stage IIB | 1.55 (0.696-3.436) | | 1.396 (0.627-3.111) | |
| Adjuvant Chemotherapy | No | 1 | 0.647 | 1 | 0.605 |
| | Yes | 0.807 (0.322-2.021) | | 0.783 (0.310-1.979) | |
| Chromatin Modifying Genes* | Wild Type | 1 | 0.012 | 1 | 0.003 |
| | Mutant | 0.222 (0.068-0.722) | | 0.210 (0.075-0.591) | |

*Includes mutation in any MLL gene for the first two columns and in any MLL gene or *ARID1A* for the last two columns

GENOMIC ALTERATIONS IN THE TUMOR AND CIRCULATION OF PANCREATIC CANCER PATIENTS

CROSS-REFERENCE TO RELATED APPLICATIONS

This application is a National Stage application under 35 U.S.C. § 371 of International Application No. PCT/US2016/018450, filed Feb. 18, 2016, which claims the benefit of U.S. Provisional Application No. 62/118,604, filed Feb. 20, 2015. The disclosures of the prior applications are incorporated by reference in their entirety.

This invention was made with government support under CA12113 and CA62924 awarded by National Institutes of Health. The government has certain rights in the invention.

TECHNICAL FIELD OF THE INVENTION

This invention is related to the area of cancer. In particular, it relates to pancreatic cancer.

BACKGROUND OF THE INVENTION

Worldwide, over 250,000 patients develop pancreatic ductal adenocarcinoma every year and the vast majority die of their disease[1]. Several genetic alterations have been identified in pancreatic cancers, including those in the CDKN2A, SMAD4 and TP53 tumor suppressor genes, and in the KRAS oncogene[2,3]. Although the discoveries of these genes and their pathways have provided important insights into the natural history of pancreatic cancer and have spurred efforts to develop improved diagnostic and therapeutic agents, few genetic alterations discovered to date in pancreatic cancer have been used to directly affect clinical care[4,5].

There is a continuing need in the art to develop tools for detecting disease, assessing disease, and effectively treating disease, particularly highly lethal disease such as pancreatic cancers.

SUMMARY OF THE INVENTION

According to one aspect of the invention a method is provided for characterizing a pancreatic adenocarcinoma. A sample of nucleic acids from a pancreatic adenocarcinoma of a human is tested to identify a somatic mutation in a chromatin regulating gene selected from the group consisting of MLL, MLL2, MLL3, and ARID1A.

Another aspect of the invention is a method for testing a human. Plasma of a human collected at the time of diagnosis of a pancreatic adenocarcinoma is tested for the presence of cell-free tumor DNA. The cell-free tumor DNA contains a somatic mutation present in the pancreatic adenocarcinoma but not present in tissues that are not pancreatic adenocarcinoma.

An additional aspect of the invention is a method for testing a human. Plasma of a human collected after surgical resection of a pancreatic adenocarcinoma is tested for the presence of cell-free tumor DNA. The cell-free tumor DNA contains a somatic mutation present in the pancreatic adenocarcinoma but not present in tissues that are not pancreatic adenocarcinoma.

One aspect of the invention is a probe or primer specific for a mutant chromatin regulating MLL (chromosome 11), MLL2 (chromosome 12), MLL 3 (chromosome 7) or ARID1A gene, said probe or primer comprising a mutation selected from the group consisting of:

ARID1A mutations:

| | | | |
|---|---|---|---|
| chr1_26928798-26928798_C_T | 403Q > X | Substitution | Nonsense; |
| chr1_26979465-26979465_C | NA | Insertion | Frameshift; |
| chr1_26978312-26978312_A_G | 1779E > G | Substitution | Nonsynonymous coding; |
| chr1_26978589-26978589_C_G | 1871H > Q | Substitution | Nonsynonymous coding; |
| chr1_26895595-26895595_GGC | 38E > EA | Insertion | In-frame insertion; |
| chr1_26960135-26960135_C_T | 708Q > X | Substitution | Nonsense; |
| chr1_26973560-26973560_G_A | 1419A > T | Substitution | Nonsynonymous coding; |
| chr1_26974706-26974706_C_A | 1682A > E | Substitution | Nonsynonymous coding; |
| chr1_26972534-26972534_C_T | 1276R > X | Substitution | Nonsense; |
| chr1_26978518-26978518_G_ | NA | Deletion | Frameshift; |
| chr1_26979254-26979254_TT | NA | Insertion | Frameshift; | and MLL (chromosome 11), MLL2 (chromosome 12), or MLL 3 (chromosome 7) mutations:

| | | | |
|---|---|---|---|
| chr7_151490485-151490485_C_G | 3704V > L | Substitution | Nonsynonymous coding; |
| chr11_117854039-117854039_G_C | 1161C > S | Substitution | Nonsynonymous coding; |
| chr11_117847769-117847769_C_A | 229P > T | Substitution | Nonsynonymous coding; |
| chr12_47718147-47718147_G_A | 3087R > W | Substitution | Nonsynonymous coding; |
| chr7_151515732-151515732_C_T | NA | Substitution | Splice site donor; |
| chr12_47729834-47729834_A | NA | Insertion | Frameshift; |
| chr7_151576224-151576224_G_A | 743P > L | Substitution | Nonsynonymous coding; |
| chr7_151476195-151476195_G_A | 4584R > W | Substitution | Nonsynonymous coding; |
| chr7_151686622-151686622_TC | NA | Insertion | Frameshift; |
| chr12_47711653-47711653_T | NA | Insertion | Frameshift; |
| chr12_47731362-47731362_G_ | NA | Deletion | Frameshift; |
| chr7_151601824-151601824_T | NA | Insertion | Frameshift; |
| chr12_47722327-47722327_G_A | 1974T > M | Substitution | Nonsynonymous coding; and |
| chr7_151510210-151510210_G_A | 1890R > X | Substitution | Nonsense. |

These and other embodiments which will be apparent to those of skill in the art upon reading the specification provide the art with

BRIEF DESCRIPTION OF THE DRAWINGS

(FIG. 2A) Representation of the mutations identified in chromatin modifying and other recurrently mutated genes. Each patient sample is indicated as a grey box with mutations indicated in green or black. (FIG. 2B) Analyses of overall survival revealed that patients wild type for MLL gene alterations (n=87) had a significantly lower median survival compared with those with mutated MLL genes (n=14; median survival 15.3 months vs not reached respectively, p=0.0063, log-rank test). (FIG. 2C) Similar analyses revealed significantly improved survival in patients with mutations in either MLL or ARID1A genes (n=20) compared with those that were wild-type for any of these genes (n=81).

(FIG. 3A) Patients with detectable circulating tumor DNA (ctDNA) after surgical resection were more likely to relapse and die from disease compared to those with undetectable ctDNA. The median time to recurrence was 9.9 months for individuals with detectable ctDNA and was not reached for those without detectable ctDNA. (FIG. 3B) Comparison between the time to detection of recurrence using ctDNA and standard-of-care CT imaging revealed that the median time to recurrence was 71 days for individuals with detectable ctDNA and 289 days for those patients with positive imaging results (p=0.0004, paired t-test).

FIG. 4 (Table 1) Clinical Actionability of Genetic Alterations in Pancreatic Cancer FIG. 5. (Supplementary FIG. 1.) Schematic of Mutations in MLL and ARID1A Proteins. Domains indicated in the schematic represent PHD, plant homeo domain finger, HMG, high mobility group box, FYRN, FY-rich N-terminal domain, FY-rich C-terminal domain, SET, Su (var)3-9 Enhancer-of-zeste Trithorax methyltransferase domain, BROM, bromodomain, ARID, ARID/BRIGHT DNA binding domain, DUF3518, and Domain of unknown function (DUF3518). Mutations were assessed for conservation by phyloP across 44 vertebrate species and those highlighted in green were predicted to be conserved. Black arrows indicate missense alterations and red arrows indicate truncating alterations.

FIG. 6A: The hazard ratio for tumor recurrence among individuals with mutant MLL, MLL2, or MLL3 genes compared to those with wild-type MLL, MLL2, or MLL3 genes (WT) was 0.54 (95% CI=0.30-0.98). The median time to recurrence was 10.2 months for individuals wild-type for MLL gene alterations and 24.9 months for those with mutated MLL genes. FIG. 6B: The hazard ratio for tumor recurrence among individuals with mutant chromatin regulator genes compared to those with wild-type (WT) chromatin regulator genes was 0.47 (95% CI=0.27-0.82). The median time to recurrence was 8.2 months for individuals wild-type for chromatin regulator gene alterations and 24.9 months for those with mutated chromatin regulator genes.

FIG. 8 (Supplemental Table 1)

FIG. 9 (Supplemental Table 4 (ARID1A, MLL, MLL2, AND MLL3)

FIG. 10 (Supplemental Table 5)

FIG. 11 (Supplemental Table 7)

FIG. 12 (Supplemental Table 8)

DETAILED DESCRIPTION OF THE INVENTION

Figure 1:
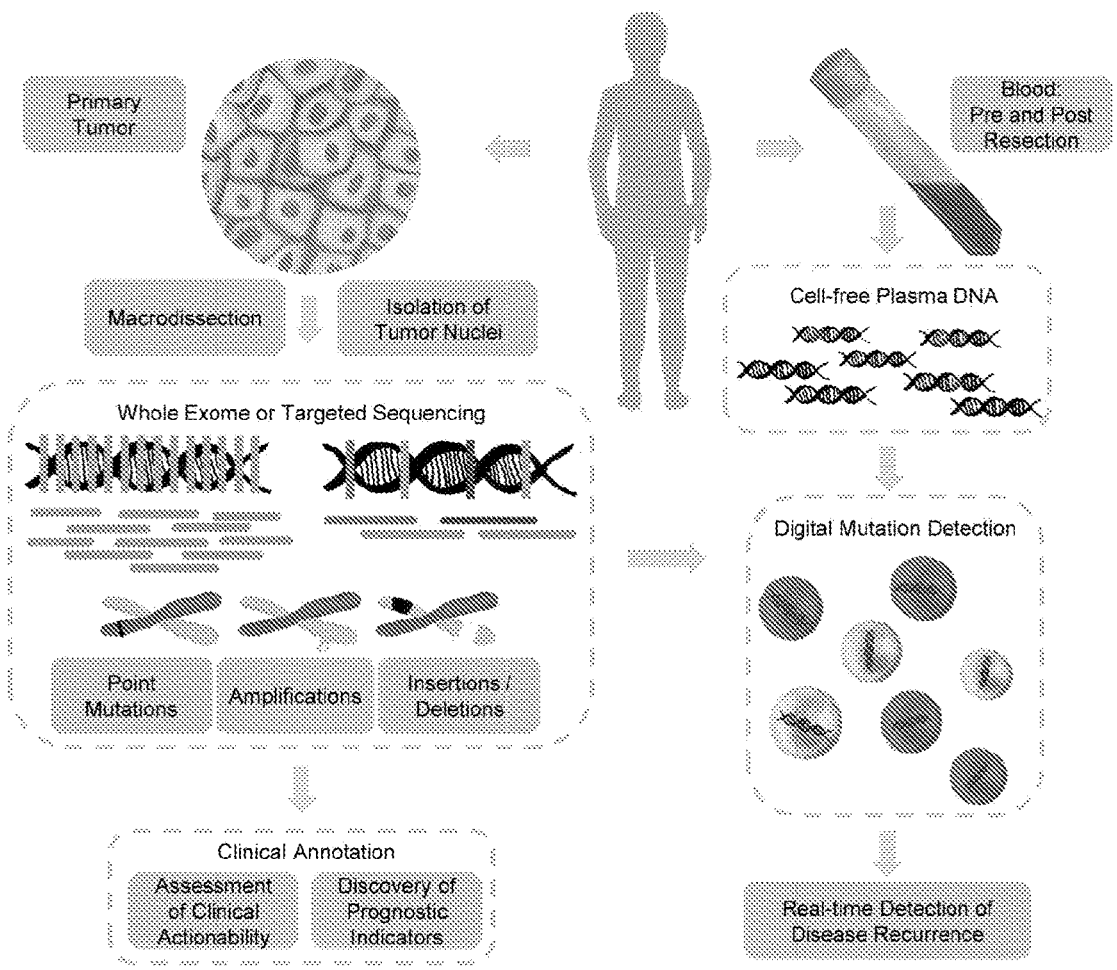
FIG. 1. Schematic of next-generation sequencing and circulating tumor DNA analyses.

Through integrated genomic analyses we have identified MLL and ARID1A genes as markers of improved prognosis, and highlighted clinically actionable alterations in genes not typically evaluated during clinical care of pancreatic cancer patients. We have also shown that cell-free DNA in the circulation of pancreatic cancer patients may provide a marker of early detection of sub-clinical, residual or recurrent disease. These analyses suggest more intensive therapies for pancreatic cancer patients without MLL or ARID1A alterations or with detectable cell-free DNA at the time of diagnosis or after surgical resection.

Testing for mutations in nucleic acids from plasma, other body fluids, or from tumor tissue can be performed by any means known in the art. Hybridization methods using probes may be used in any assay format desired, including but not limited to Southern or Northern blots, and microarrays. The probes may be double or single stranded. They may hybridize to the sense strand of the gene or the anti-sense strand. Mutations may also be detected using an amplification method, whether linear or exponential. The amplification may utilize one or more primers. The primers may be contain a mutant nucleotide or be adjacent to it. A primer pair may surround a mutant nucleotide and the detection of the mutant may rely on hybridization to a probe after amplification. Other means for identifying mutations include nucleic acid sequencing techniques. Probes and primers may be labeled with any detectable label known in the art, including but not limited to radionuclides, fluorescent labels, chromophores, enzymes. Probes or primers may contain non-naturally occurring components, for example, to limit degradation. Artificial nucleic acids may include peptide nucleic acid, morpholino and locked nucleic acid, glycol nucleic acid, and threose nucleic acid (TNA). Each of these is distinguished from naturally occurring DNA or RNA by changes to the backbone of the molecule.

Nucleic acids from pancreatic adenocarcinomas may be obtained from biopsies or from surgical samples. Nucleic acids found in the plasma of a patient with a tumor are believed to be shed into the circulation or other body fluids, perhaps by cells which are undergoing apoptosis or necrosis. The presence of a somatic mutation that is identical to one found in the tumor indicates that the nucleic acid ultimately derived from the tumor.

Control nucleic acids for determining a somatic mutation may be taken from any normal tissue, including normal portions of the patient's pancreas, or other organs. If a mutation is a germline mutation, it will be found in all of a patient's tissues. In the case of circulating tumor DNA found in the plasma, this DNA typically forms a minority of the DNA found in the plasma.

Mutations that affect a coding sequence include substitutions, insertions, and deletions. These may cause nonsense, frameshifts, splice site donor, or non-synonymous coding mutations. Other than the latter type, these mutation types will typically lead to truncation of an encoded message or product.

Plasma, other body fluid, and/or tissue samples can be collected for testing at the time of diagnosis, before surgical resections, or after surgical resections. The findings of mutations or no mutations can inform subsequent treatment options. In some cases, surgery may be averted if a good prognosis is determined. In other cases more intensive therapies may be used to counter a bad prognostic finding. In other cases less intensive therapies may be used when a favorable prognostic indication is found. Therapies may be more or less intensive in kind, dosage, or duration.

The finding of mutations in the chromatin regulation genes is a positive prognostic indicator. Finding of tumor-specific, cell-free DNA is a negative prognostic indicator. Conversely, finding of no tumor-specific, cell-free DNA can be considered a positive prognostic indicator and finding of no chromatin regulation gene mutations may be considered a negative prognostic indicator. These factors affect both disease-free progression time as well as overall survival time. Prognoses can be delivered to a patient in a written or electronic form. They can be delivered from a clinical laboratory to a practicing physician.

Cell-free tumor DNA can be tested for mutations in any genes that are known to be associated with cancers. Often a single patient will have many somatic mutations in his tumor. Any of these can be detected and followed in the cell-free DNA of the plasma or other body fluid. Frequently mutated genes in pancreatic adenocarcinomas include KRAS, BRAF, and PIK3CA. Other frequently mutated genes may be monitored.

Plasma or other body fluids may be tested for the presence of cell-free DNA. Suitable body fluids include serum, blood, pancreatic juice, pus, stool, etc. Drainage of pancreatic lesions into the stomach or jejunum may lead to increased cell-free pancreatic DNA in the stool.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1-Materials and Methods

Samples Obtained for Sequencing Analyses

Pancreatic ductal adenocarcinoma tumor specimens and matched germline specimens (from peripheral blood) from 101 patients were used for genomic analyses. Plasma samples were obtained at the time of diagnosis from 44 of these patients as well as 7 additional patients. Informed consent for research use was obtained from all patients at the enrolling institution prior to tissue banking and study approval was obtained. Primary tumor samples for genomic analyses were selected from patients with resectable stage II disease, verified to have ≥10% viable tumor cell content by histopathological assessment, and demonstrated to be wild-type for the DAXX/ATRX loci, which have been shown to be associated with improved outcome in patients with pancreatic neuroendocrine tumors)). For a subset of cases, plasma samples were obtained at multiple time points after surgery.

Flow-Sorting of Aneuploid Nuclei

Flow sorting of tumor nuclei: Individual biopsies were minced with scalpel blades in a petri dish (35×100 mm) in NST buffer (146 mM NaCl, 10 mM Tris-HCl, pH 7.5, 1 mM CaCl2, 0.5 mM MgSO4, 21 mM MgCl2, 0.05% bovine serum albumin, 0.2% Nonidet P40 (Sigma)) with 4,6-diamindino-2-phenylindole (DAPI; 10 µg/ml; Boehringer) according to published protocols (Ruiz, Lenkiewicz et al. 2011). The nuclei were then disaggregated with a 25-gauge needle, and subsequently filtered through a 40-µm mesh filter immediately before analyses on an Influx cytometer (Becton-Dickinson, San Jose Calif.), with ultraviolet excitation and DAPI emission collected at >450 nm. We sorted all diploid, aneuploid, and tetraploid fractions from each sample. DNA content and cell cycle were analyzed using the software program MultiCycle (Phoenix Flow Systems, San Diego, Calif.).

Sample Preparation and Next-Generation Sequencing

Sample preparation, library construction, exome and targeted capture, next generation sequencing, and bioinformatics analyses of tumor and normal samples were performed as previously described. In brief, DNA was extracted from frozen or formalin-fixed paraffin embedded (FFPE) tissue, along with matched blood or saliva samples using the Qiagen DNA FFPE tissue kit or Qiagen DNA blood mini kit (Qiagen, CA). Genomic DNA from tumor and normal samples were fragmented and used for Illumina TruSeq library construction (Illumina, San Diego, Calif.) according to the manufacturer's instructions or as previously described 17. Briefly, 50 nanograms (ng)-3 micrograms (µg) of genomic DNA in 100 microliters (µl) of TE was fragmented in a Covaris sonicator (Covaris, Woburn, Mass.) to a size of 150-450 bp. To remove fragments smaller than 150 bp, DNA was purified using Agencourt AMPure XP beads (Beckman Coulter, IN) in a ratio of 1.0 to 0.9 of PCR product to beads twice and washed using 70% ethanol per the manufacturer's instructions. Purified, fragmented DNA was mixed with 36 µl of H2O, 10 µl of End Repair Reaction Buffer, 5 µl of End Repair Enzyme Mix (cat# E6050, NEB, Ipswich, Mass.). The 100 µl end-repair mixture was incubated at 20° C. for 30 min, and purified using Agencourt AMPure XP beads (Beckman Coulter, IN) in a ratio of 1.0 to 1.25 of PCR product to beads and washed using 70% ethanol per the manufacturer's instructions. To A-tail, 42 µl of end-repaired DNA was mixed with 5 µl of 10× dA Tailing Reaction Buffer and 3 µl of Klenow (exo-)(cat# E6053, NEB, Ipswich, Mass.). The 50 µl mixture was incubated at 37° C. for 30 min and purified using Agencourt AMPure XP beads (Beckman Coulter, IN) in a ratio of 1.0 to 1.0 of PCR product to beads and washed using 70% ethanol per the manufacturer's instructions. For adaptor ligation, 25 µl of A-tailed DNA was mixed with 6.7 µl of H2O, 3.3 µl of PE-adaptor (Illumina), 10 µl of 5× Ligation buffer and 5 µl of Quick T4 DNA ligase (cat# E6056, NEB, Ipswich, Mass.). The ligation mixture was incubated at 20° C. for 15 min and purified using Agencourt AMPure XP beads (Beckman Coulter, IN) in a ratio of 1.0 to 0.95 and 1.0 of PCR product to beads twice and washed using 70% ethanol per the manufacturer's instructions. To obtain an amplified library, twelve PCRs of 25 µl each were set up, each including 15.5 µl of H2O, 5 µl of 5× Phusion HF buffer, 0.5 µl of a dNTP mix containing 10 mM of each dNTP, 1.25 µl of DMSO, 0.25 µl of Illumina PE primer #1, 0.25 µl of Illumina PE primer #2, 0.25 µl of Hotstart Phusion polymerase, and 2 µl of the DNA. The PCR program used was: 98° C. for 2 minutes; 12 cycles of 98° C. for 15 seconds, 65° C. for 30 seconds, 72° C. for 30 seconds; and 72° C. for 5 min. DNA was purified using Agencourt AMPure XP beads (Beckman Coulter, IN) in a ratio of 1.0 to 1.0 of PCR product to beads and washed using 70% ethanol per the manufacturer's instructions. Exonic or targeted regions were captured in solution using the Agilent SureSelect v.4 kit or a custom targeted panel for the 111 genes of interest according to the manufacturer's instructions (Agilent, Santa Clara, Calif.). The captured library was then purified with a Qiagen MinElute column purification kit and eluted in 17 µl of 70° C. EB to obtain 15 µl of captured DNA library. (5) The captured DNA library was amplified in the following way: Eight 30 uL PCR reactions each containing 19 µl of H2O, 6 µl of 5× Phusion HF buffer, 0.6 µl of 10 mM dNTP, 1.5 μl of DMSO, 0.30 μl of Illumina PE primer #1, 0.300 of Illumina PE primer #2, 0.30 μl of Hotstart Phusion polymerase, and 2 μl of captured exome library were set up. The PCR program used was: 98° C. for 30 seconds; 14 cycles (exome) or 16 cycles (targeted) of 98° C. for 10 seconds, 65° C. for 30 seconds, 72° C. for 30 seconds; and 72° C. for 5 min. To purify PCR products, a NucleoSpin Extract II purification kit (Macherey-Nagel, PA) was used following the manufacturer's instructions. Paired-end sequencing, resulting in 100 bases from each end of the fragments for exome libraries and 150 bases from each end of the fragment for targeted libraries, was performed using Illumina HiSeq 2000/2500 and Illumina MiSeq instrumentation (Illumina, San Diego, Calif.).

Primary Processing of Next-Generation Sequencing Data and Identification of Putative Somatic Mutations Somatic mutations were identified using VariantDx custom software for identifying mutations in matched tumor and normal samples through Personal Genome Diagnostics (Baltimore, Md.). Prior to mutation calling, primary processing of sequence data for both tumor and normal samples were performed using Illumina CASAVA software (v1.8), including masking of adapter sequences. Sequence reads were aligned against the human reference genome (version hg18) using ELAND with additional realignment of select regions using the Needleman-Wunsch method 18. Candidate somatic mutations, consisting of point mutations, insertions, and deletions were then identified using VariantDx across the either the whole exome or regions of interest. VariantDx examines sequence alignments of tumor samples against a matched normal while applying filters to exclude alignment and sequencing artifacts. In brief, an alignment filter was applied to exclude quality failed reads, unpaired reads, and poorly mapped reads in the tumor. A base quality filter was applied to limit inclusion of bases with reported phred quality score >30 for the tumor and >20 for the normal. A mutation in the tumor was identified as a candidate somatic mutation only when (i) distinct paired reads contained the mutation in the tumor; (ii) the number of distinct paired reads containing a particular mutation in the tumor was at least 2% of the total distinct read pairs for targeted analyses and 10% of read pairs for exome and (iii) the mismatched base was not present in >1% of the reads in the matched normal sample as well as not present in a custom database of common germline variants derived from dbSNP and (iv) the position was covered in both the tumor and normal. Mutations arising from misplaced genome alignments, including paralogous sequences, were identified and excluded by searching the reference genome. Candidate somatic mutations were further filtered based on gene annotation to identify those occurring in protein coding regions. Functional consequences were predicted using snpEff and a custom database of CCDS, RefSeq and Ensembl annotations using the latest transcript versions available on hg18 from UCSC (https://genome.ucsc.edu/). Predictions were ordered to prefer transcripts with canonical start and stop codons and CCDS or Refseq transcripts over Ensembl when available. Finally mutations were filtered to exclude intronic and silent changes, while retaining mutations resulting in missense mutations, nonsense mutations, frameshifts, or splice site alterations. A manual visual inspection step was used to further remove artifactual changes.

Identification of Putative Somatic Mutations without Matched Normal Sample

For the identification of putative somatic mutations without a matched normal, additional filters were applied. Firstly, mutations present in an unmatched normal sample, sequenced to a similar coverage and on the same platform as the matched normal, were removed. Second, alterations reported in the 1000 Genomes project, present in >1% of the population or listed as Common in dbSNP138 were filtered.

Clinical Actionability Analyses

We selected 200 well characterized genes with potential clinical significance and assessed the level of evidence for clinical actionability in three ways. Firstly, we determined which of the genes were associated with FDA approved therapies (see URL www.fda.gov/Drugs/). Secondly, we carried out a literature search to identify published prospective clinical studies pertaining to genomic alterations of each gene and their association with outcome for cancer patients. Genes that served as targets for specific agents or were predictors of response or resistance to cancer therapies when mutated were considered actionable. Thirdly, we identified clinical trials (see URL www.clinicaltrials.gov) that specified altered genes within the inclusion criteria and were actively recruiting patients in August 2014. In all cases, the tumor type relevant to the FDA approval or studied in the clinical trials was determined to allow the clinical information to be matched to the mutational data by both gene and cancer type.

Statistical Analyses for Clinical and Genetic Data

Unpaired T-test and chi-square were employed to compare mutation status of MLL genes among different groups with different clinical and pathological characteristics. Curves for overall survival and progression free survival (calculated as the time from diagnosis to disease progression) were constructed using the Kaplan-Meier method and compared between groups using the log-rank test. Cox proportional hazards regression analysis was used to determine which independent factors jointly had a significant impact on overall survival. All p values were based on 2-sided testing and differences were considered significant at p<0.05. Passenger probabilities were calculated using the binomial test adjusted for gene sizes and corrected for multiple comparisons. Genes which were recurrently mutated within the comprehensive exome analysis (≥2 cases) were considered. Statistical analyses of clinical and genetic features were performed with SPSS version 22 for windows, while conservation of specific genomic positions were evaluated using phyloP software[23].

Digital PCR Analyses

KRAS, BRAF, or PIK3CA somatic point mutations were identified through sequencing analysis of tumor tissues. In cases with matched plasma samples, point mutations were detected in the plasma using droplet digital PCR (ddPCR) using the BioRad QX200™ Droplet Digital™ PCR System (Hercules, Calif.). Briefly, specific ddPCR assays for each point mutation were obtained from BioRad (Hercules, Calif.) and applied to assess the mutant allele fraction (mutant genomic equivalents/total genomic equivalents). Prior to analysis of each point mutation in the patient plasma sample, a panel of at least 160 normal control analyses were used to confirm the mutation specificity of the assay. Additionally, control samples of wild-type DNA were included in each analysis.

Example 2

In order to identify genetic alterations that may be related to patient outcome and other clinical characteristics, we performed large-scale genomic analyses of pancreatic adenocarcinomas using two prospectively collected clinical cohorts.

We used next generation sequencing to examine the entire exomes of matched tumor-normal specimens from 24 patients and targeted sequencing to analyze an additional 77 patient tumors. These approaches allowed us to identify sequence changes, including single base and small insertion or deletion mutations, as well as copy number alterations in >20,000 genes in the whole-exome analyses and in 116 specific genes in the targeted analyses (Supplementary Table 1). The pancreatic cancers analyzed were stage II tumors in patients who underwent potentially curative resections. Given the low neoplastic cellularity of pancreatic cancers[2], we enriched for neoplastic cells either by macrodissecting primary tumors or by flow-sorting tumor nuclei (example 1), and performed high-coverage sequencing of these enriched samples. We obtained a per-base sequencing coverage of 234-fold for each tumor analyzed by whole-exome sequencing and 754-fold for each tumor analyzed by targeted cancer gene sequencing (Example 1).

We detected an average of 114 tumor-specific (somatic) non-synonymous sequence alterations in the cancers analyzed by whole exome sequencing, similar to previous studies of this tumor type[2,3], and 4.7 non-synonymous sequence alterations per cancer in the targeted analyses (Supplementary Table 4). Among known recurrent sequence alterations in the cancers analyzed we identified mutations in the known pancreatic cancer driver genes: KRAS (88%), TP53 (77%), SMAD4 (29%), CDKN2A (18%), and TGFBR2 (7%) (Supplementary Tables 4 and 5)[2,3]. Homozygous deletions were difficult to assess given the low purity of the samples, but such alterations were identified in CDKN2A in an additional 5% of cases.

We also identified recurrent somatic alterations in genes involved in chromatin regulation or modification, primarily involving the AT-rich interactive domain-containing ARID1A gene (9% of cases) and the histone methyltransferase MLL3 gene (7%) (Supplementary FIG. 1, Supplementary Tables 4 and 5)[6]. Six of the alterations in ARID1A were either nonsense or frameshift alterations which were predicted to truncate the protein (Supplementary Table 4, Supplementary FIG. 1). Mutations in the MLL3 gene included a combination of nonsynonymous, nonsense, frameshift and splice-site mutations which occurred in amino acids predicted to be evolutionarily conserved (Supplementary Table 4, Supplementary FIG. 1). We found somatic frameshift and nonsynonymous sequence alterations in the related methyltransferases MLL or MLL2 in eight additional cases. Interestingly, no tumor had more than one gene mutated among the MLL genes suggesting that mutation in any one may be sufficient to confer a selective advantage in neoplastic cells.

Example 3

Figure 2:
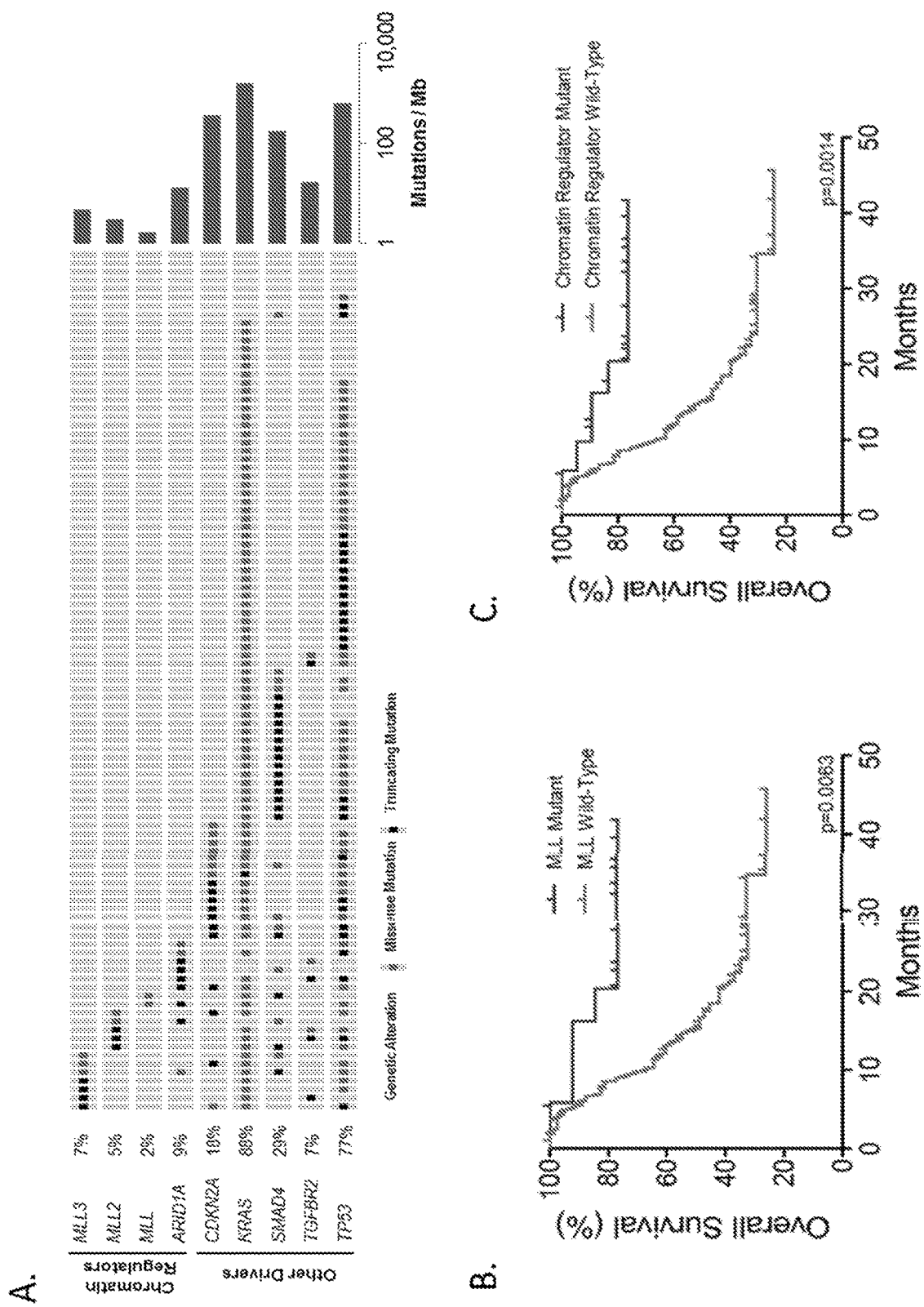
FIG. 2A-2C. Recurrent genetic alterations in pancreatic cancer and their effect on disease outcome.

Given the global cellular changes regulated by chromatin regulators[7,8] we examined the survival characteristics of patients with mutations in either the MLL or ARID1A genes and found that patients with MLL alterations had a prolonged survival compared to those that were wild-type at these loci. Over three quarters (79%) of patients with mutations in MLL, MLL2 or MLL3 were still alive at the time of the analysis (median follow-up of 32 months), while the median survival in patients with wild-type sequences of these genes was 15.3 months (p=0.0063; log-rank test, FIG. 2 and Supplementary FIG. 2). MLL mutation status was independent of clinical characteristics (Supplementary Table 7, p>0.05 for all comparisons by chi-square and unpaired t-test) and was found to be an independent prognostic factor (Supplementary Table 8, p=0.015, Cox multivariate regression analysis). Patients with alterations in ARID1A had improved survival (p<0.05, log-rank test) but this observation was limited by a shorter follow-up time in affected individuals. Patients with mutations in any of the chromatin regulating genes identified had prolonged overall and progression-free survival and these observations were independent of other clinical variables (p<0.01 for all analyses, FIG. 2, Supplementary FIG. 2, and Supplementary Table 8). Genomic analyses in other tumor types have shown that somatic mutations of epigenetic regulators can have important clinical consequences, including improved outcome in patients with DAXX/ATRX alterations in pancreatic neuroendocrine tumors[9], and a decreased survival in patients with ARID1A and ARID1B mutations in neuroblastoma[10].

Example 4

In parallel to the sequencing analyses of neoplastic tissues, we evaluated the utility of using somatic mutations in circulating tumor DNA (ctDNA) to identify patients likely to recur after surgical intervention. Through sequencing analyses of tumor samples we identified somatic mutations that could be used to detect ctDNA in 51 patients from whom plasma was available, largely focusing on alterations in the KRAS, BRAF and PIK3CA genes (Online Methods). Using digital polymerase chain reaction (dPCR) approaches, we were able to demonstrate that these alterations were detectable in the plasma of 22 patients (43%) at the time of diagnosis, with a specificity of >99.9% (Example 1). Consistent with recent reports[11,12], these results suggest that a significant fraction of early stage pancreatic cancers could be diagnosed non-invasively using approaches that focus on a few specific genetic alterations.

Figure 3:
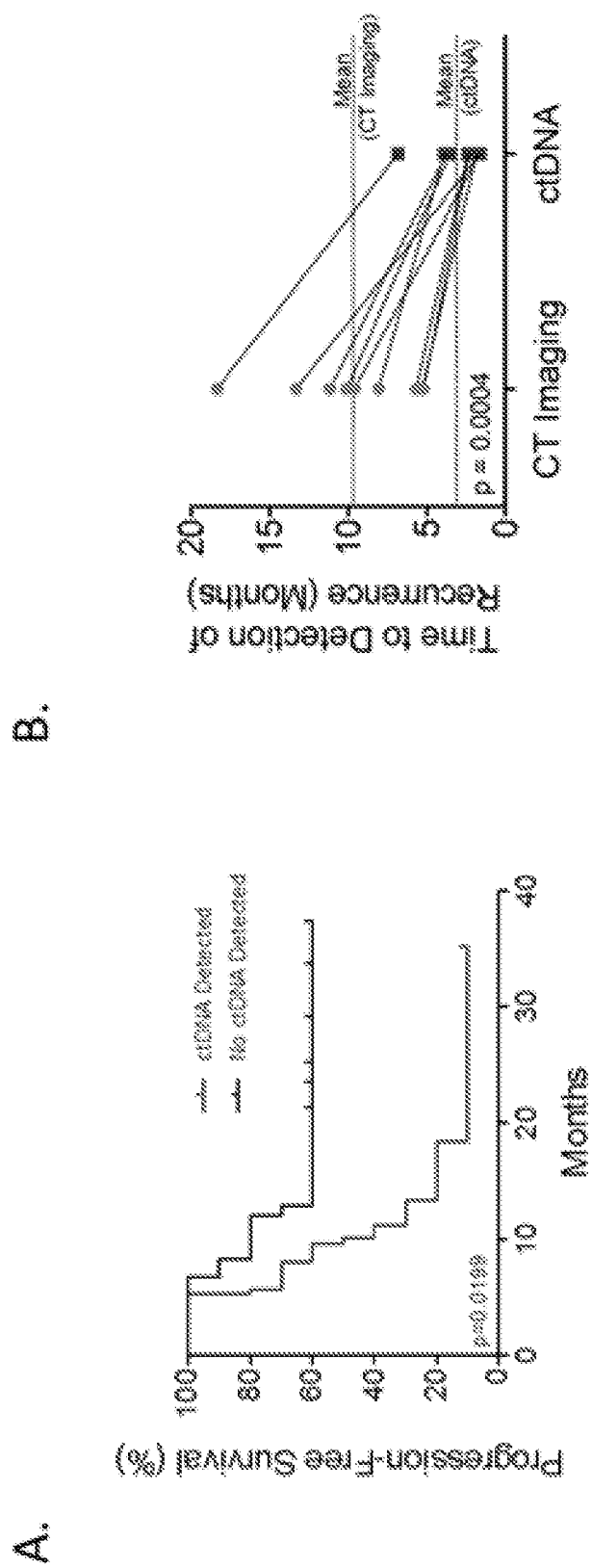
FIG. 3A-3B. Detection of residual disease using CT imaging and ctDNA analyses.
Figure 5:
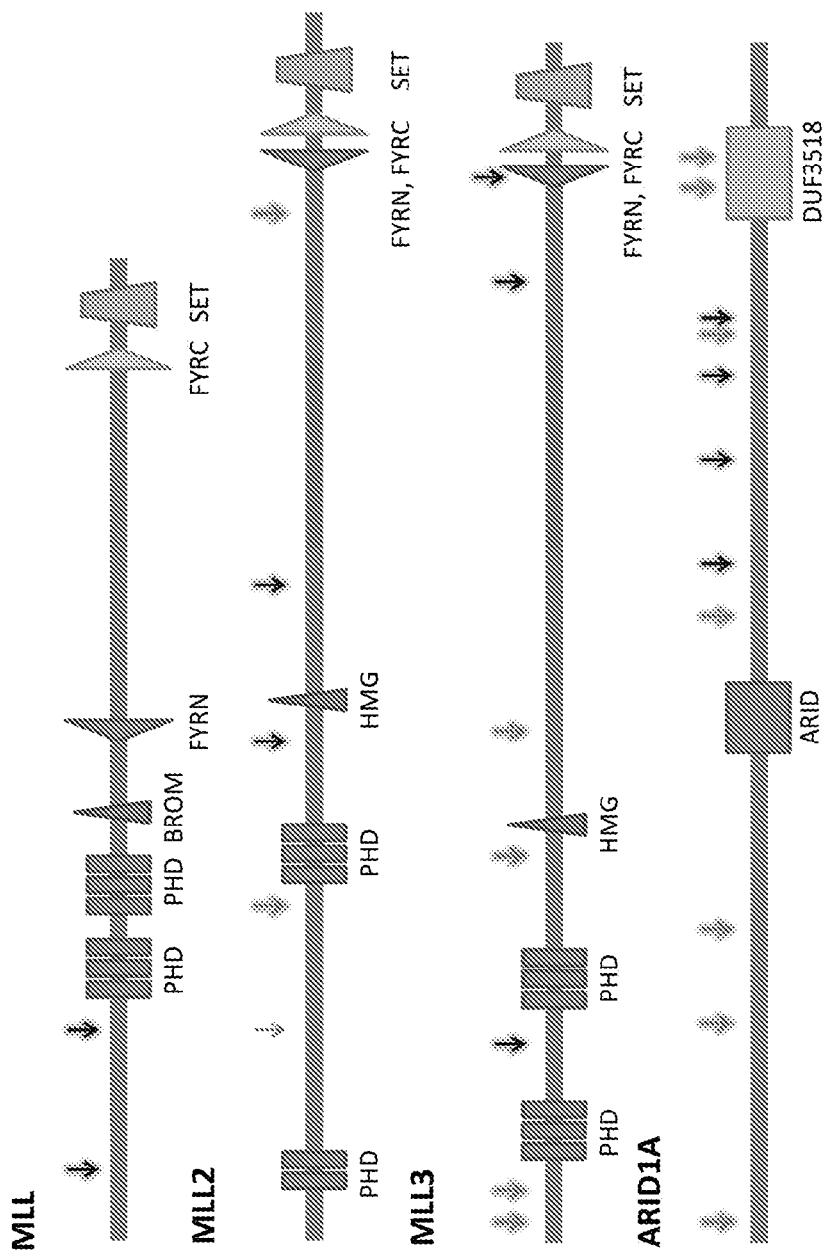
Figures 6A, 6B:
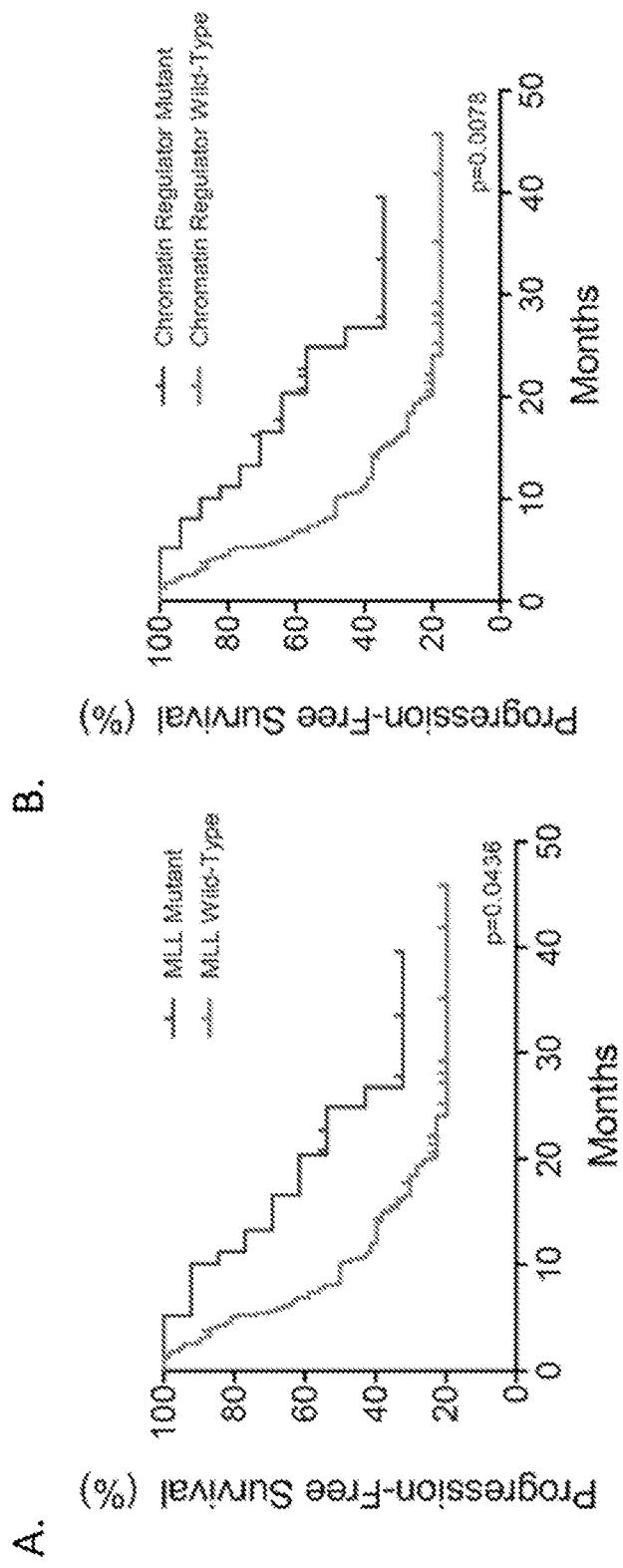
FIG. 6A-6B. (Supplementary FIG. 2.) Kaplan Meier Progression-Free Survival Analysis of MLL and Chromatin Regulator Mutations.
Figure 7:
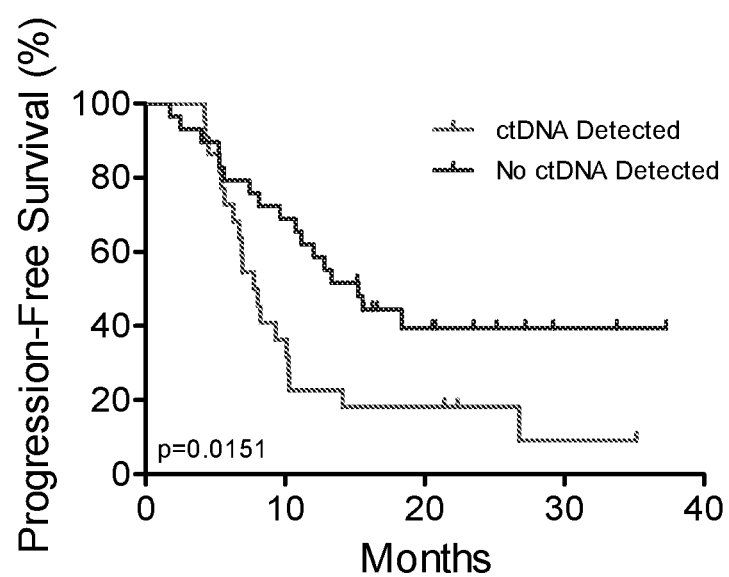
FIG. 7. (Supplementary FIG. 3.) Prediction of Recurrence using ctDNA Detected at Baseline. The hazard ratio for tumor recurrence among individuals with detectable circulating tumor DNA (ctDNA) compared to those without detectable ctDNA was 2.39 (95% CI=1.18-4.81). The median time to recurrence was 15.2 months for individuals without detectable ctDNA and 7.9 months for those with detectable ctDNA.

Example 5 dPCR analyses were performed using plasma samples obtained at various time points after surgical resection. These analyses revealed that patients with detectable ctDNA in their plasma were more likely to relapse than those with undetectable alterations (p=0.02, log-rank test, FIG. 3a). Disease progression using ctDNA was detected at an average of 3.1 months after surgery compared to 9.6 months using standard CT imaging (p=0.0004, paired t-test, FIG. 3b). The presence of ctDNA at the time of diagnosis also provided a predictor of disease recurrence (p=0.015, log-rank test, Supplementary FIG. 3). These analyses suggest that tests to detect sequence alterations in cell free DNA may provide a highly specific approach for early detection of residual or recurrent disease after surgical resection.

Example 6

Given the poor outcome and limited therapeutic options for patients with pancreatic cancer, we investigated whether mutations observed in individual cases may be clinically actionable using existing or investigational therapies. We examined genetic alterations that were associated with 1) FDA-approved therapies for oncologic indications, 2) therapies in published prospective clinical studies, and 3) ongoing clinical trials for patients with pancreatic cancer or other tumor types. We also evaluated alterations in five genes in the patients' germline that may affect cancer predisposition as detection of such changes have important implications for early detection and intervention[13].

Through these analyses we were able to identify somatic alterations with potentially actionable consequences in 98 of the 101 patients (97%) (Table 1, Supplementary Table 10). Even if one excludes clinical trials related to alterations in KRAS and TP53, over a third (38%) of patients had clinically actionable mutations (Table 1). These alterations included amplification of the HER-2/neu tyrosine kinase ERBB2, the serine and threonine kinases AKT1 and AKT2 genes, the cyclin dependent kinase CDK4 gene, and the E3 ubiquitin ligase MDM2 gene. We also observed nonsynonymous somatic mutations in the catalytic domains of the phosphatidylinositol-4,5-bisphosphate 3-kinase, PIK3CA, and the v-kit Hardy-Zuckerman 4 feline sarcoma viral oncogene homolog, KIT (Supplementary Table 4). These alterations were at or nearby previously identified somatic mutations in other human cancers[14]. In addition, we identified three patients with truncating somatic alterations in BRCA2: two with heterozygous somatic nonsense alterations, a patient with a frameshift alteration, and a fourth patient with a germline frameshift in BRCA2 together with a loss of heterozygosity (LOH) in the matched-tumor sample (Supplementary Table 4).

These alterations represent potential targets of clinical intervention in pancreatic cancer. Poly(adenosine diphosphate [ADP]-ribose) polymerase (PARP) inhibitors and DNA damaging agents such as cisplatin and mitomycin C have been shown to provide a synthetic lethal therapeutic strategy for treatment of cancers with defects in components of the homologous recombination repair pathway, such as BRCA1/2[15-18]. Trastuzumab has demonstrated therapeutic efficacy against GI tumors with ERBB2 amplification[19] and is currently being evaluated in clinical trials for patients with metastatic colorectal cancer[20]. Small molecule inhibitors have been reported that target proteins or the pathways encoded by the altered genes identified, including PIK3CA, BRAF, AKT1/AKT2, and MDM2, but these not been evaluated in pancreatic cancer.

This study highlights information that may be obtained through the integration of large-scale genomic and clinical analyses in pancreatic cancer. Although careful measures were taken to increase sensitivity of detecting genetic changes in the tumors and in the circulation of these patients, some alterations may not have been detected due to low tumor purity, limited plasma amounts, and low mutant allele frequency. Despite these limitations, these data add to our growing understanding of pancreatic cancer.

REFERENCES

The disclosure of each reference cited is expressly incorporated herein.
1. Siegel, R. L., Miller, K. D. & Jemal, A. Cancer statistics, 2015. *CA Cancer J Clin* 65, 5-29 (2015).
2. Biankin, A. V. et al. Pancreatic cancer genomes reveal aberrations in axon guidance pathway genes. *Nature* 491, 399-405 (2012).
3. Jones, S. et al. Core signaling pathways in human pancreatic cancers revealed by global genomic analyses. *Science* 321, 1801-6 (2008).
4. Paulson, A. S., Tran Cao, H. S., Tempero, M. A. & Lowy, A. M. Therapeutic advances in pancreatic cancer. *Gastroenterology* 144, 1316-26 (2013).
5. Siegel, R., Naishadham, D. & Jemal, A. Cancer statistics, 2013. *CA Cancer J Clin* 63, 11-30 (2013).
6. Jones, S. et al. Somatic mutations in the chromatin remodeling gene ARID1A occur in several tumor types. *Hum Mutat* 33, 100-3 (2012).
7. Goyama, S. & Mulloy, J. C. NF-kappaB: A Coordinator for Epigenetic Regulation by MLL. *Cancer Cell* 24, 401-2 (2013).
8. Popovic, R. & Licht, J. D. Emerging epigenetic targets and therapies in cancer medicine. *Cancer Discov* 2, 405-13 (2012).
9. Jiao, Y. et al. DAXX/ATRX, MEN1, and mTOR pathway genes are frequently altered in pancreatic neuroendocrine tumors. *Science* 331, 1199-203 (2011).
10. Sausen, M. et al. Integrated genomic analyses identify ARID1A and ARID1B alterations in the childhood cancer neuroblastoma. *Nat Genet* 45, 12-7 (2013).
11. Bettegowda, C. et al. Detection of circulating tumor DNA in early- and late-stage human malignancies. *Sci Transl Med* 6, 224ra24 (2014).
12. Newman, A. M. et al. An ultrasensitive method for quantitating circulating tumor DNA with broad patient coverage. *Nat Med* 20, 548-54 (2014).
13. Iacobuzio-Donahue, C. A., Velculescu, V. E., Wolfgang, C. L. & Hruban, R. H. Genetic basis of pancreas cancer development and progression: insights from whole-exome and whole-genome sequencing. *Clin Cancer Res* 18, 4257-65 (2012).
14. Forbes, S. A. et al. COSMIC: mining complete cancer genomes in the Catalogue of Somatic Mutations in Cancer. *Nucleic Acids Res* 39, D945-50 (2011).
15. Fogelman, D. R. et al. Evidence for the efficacy of Iniparib, a PARP-1 inhibitor, in BRCA2-associated pancreatic cancer. *Anticancer Res* 31, 1417-20 (2011).
16. Fong, P. C. et al. Inhibition of poly(ADP-ribose) polymerase in tumors from BRCA mutation carriers. *N Engl J Med* 361, 123-34 (2009).
17. van der Heijden, M. S. et al. In vivo therapeutic responses contingent on Fanconi anemia/BRCA2 status of the tumor. *Clin Cancer Res* 11, 7508-15 (2005).
18. Villarroel, M. C. et al. Personalizing cancer treatment in the age of global genomic analyses: PALB2 gene mutations and the response to DNA damaging agents in pancreatic cancer. *Mol Cancer Ther* 10, 3-8 (2011).
19. Sorscher, S. M. Marked response to single agent trastuzumab in a patient with metastatic HER-2 gene amplified rectal cancer. *Cancer Invest* 29, 456-9 (2011).
20. Ramanathan, R. K. et al. Low overexpression of HER-2/neu in advanced colorectal cancer limits the usefulness of trastuzumab (Herceptin) and irinotecan as therapy. A phase II trial. *Cancer Invest* 22, 858-65 (2004).
20. Jiao, Y. et al. DAXX/ATRX, MEN1, and mTOR pathway genes are frequently altered in pancreatic neuroendocrine tumors. *Science* 331, 1199-203 (2011).
21. Jones, S. et al. Core signaling pathways in human pancreatic cancers revealed by global genomic analyses. *Science* 321, 1801-6 (2008).
22. Sausen, M. et al. Integrated genomic analyses identify ARID1A and ARID1B alterations in the childhood cancer neuroblastoma. *Nat Genet* 45, 12-7 (2013).
23. Cooper, G. M. et al. Distribution and intensity of constraint in mammalian genomic sequence. *Genome Res* 15, 901-13 (2005).

We claim:
1. A method for testing and treating a human comprising:
identifying the presence of cell-free tumor DNA in a plasma sample of a human collected at the time of diagnosis of a pancreatic adenocarcinoma, wherein the cell-free tumor DNA contains a somatic mutation present in the pancreatic adenocarcinoma selected from the group consisting of:

| | | | |
|---|---|---|---|
| chr7_151490485-151490485_C_G | 3704V > L | Substitution | Nonsynonymous coding; |
| chr7_151515732-151515732_C_T | | Substitution | Splice site donor; |
| chr7_151576224-151576224_G_A | 743P > L | Substitution | Nonsynonymous coding; |
| chr7_151476195-151476195_G_A | 4584R > W | Substitution | Nonsynonymous coding; |
| chr7_151686622-151686622_TC | | Insertion | Frameshift; |
| chr7_151601824-151601824_T | | Insertion | Frameshift; and |
| chr7_151510210-151510210_G_A | 1890R > X | Substitution | Nonsense; | wherein the somatic mutation is with respect to the reference human genome assembly hg18; and performing surgery to remove the pancreatic adenocarcinoma when the presence of the cell-free tumor DNA containing the somatic mutation is identified in the plasma sample.

2. The method of claim 1 wherein the somatic mutation is a missense mutation or a truncating mutation.

3. A method for testing and treating a human comprising: identifying the presence of cell-free tumor DNA in a plasma sample of a human collected after surgical resection of a pancreatic adenocarcinoma, wherein the cell-free tumor DNA contains a somatic mutation present in the pancreatic adenocarcinoma selected from the group consisting of:

| | | | |
|---|---|---|---|
| chr7_151490485-151490485_C_G | 3704V > L | Substitution | Nonsynonymous coding; |
| chr7_151515732-151515732_C_T | | Substitution | Splice site donor; |
| chr7_151576224-151576224_G_A | 743P > L | Substitution | Nonsynonymous coding; |
| chr7_151476195-151476195_G_A | 4584R > W | Substitution | Nonsynonymous coding; |
| chr7_151686622-151686622_TC | | Insertion | Frameshift; |
| chr12_47731362-47731362_G_ | | Deletion | Frameshift; |
| chr7_151601824-151601824_T | | Insertion | Frameshift; and |
| chr7_151510210-151510210_G_A | 1890R > X | Substitution | Nonsense; | wherein the somatic mutation is with respect to the reference human genome assembly hg18; and performing surgery to remove the pancreatic adenocarcinoma when the presence of the cell-free tumor DNA containing the somatic mutation is identified in the plasma sample.

4. The method of claim 1, wherein the identifying is performed using a nucleic acid hybridization method.

5. The method of claim 1, wherein the identifying is performed using a nucleic acid amplification method.

6. The method of claim 1, wherein the identifying is performed using a nucleic acid sequencing method.

7. The method of claim 3, wherein the identifying is performed using a nucleic acid hybridization method.

8. The method of claim 3, wherein the identifying is performed using a nucleic acid amplification method.

9. The method of claim 3, wherein the identifying is performed using a nucleic acid sequencing method.

* * * * *

UNITED STATES PATENT AND TRADEMARK OFFICE
CERTIFICATE OF CORRECTION

PATENT NO. : 10,815,522 B2
APPLICATION NO. : 15/552076
DATED : October 27, 2020
INVENTOR(S) : Victor E. Velculescu et al.

It is certified that error appears in the above-identified patent and that said Letters Patent is hereby corrected as shown below:

In the Specification

Column 1, Lines 14-16, delete "This invention was made with government support under CA12113 and CA62924 awarded by National Institutes of Health. The government has certain rights in the invention" and insert -- This invention was made with government support under grant CA121113 awarded by the National Institutes of Health. The government has certain rights in the invention. --, therefor.

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*